(12) United States Patent
Kemere et al.

(10) Patent No.: US 7,058,445 B2
(45) Date of Patent: Jun. 6, 2006

(54) DECODING OF NEURAL SIGNALS FOR MOVEMENT CONTROL

(75) Inventors: Caleb T. Kemere, Menlo Park, CA (US); Gopal Santhanam, Sunnyvale, CA (US); Byron M. Yu, San Jose, CA (US); Teresa H. Meng, Saratoga, CA (US); Krishna V. Shenoy, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 74 days.

(21) Appl. No.: 10/966,355

(22) Filed: Oct. 15, 2004

(65) Prior Publication Data

US 2005/0159668 A1    Jul. 21, 2005

Related U.S. Application Data

(60) Provisional application No. 60/512,292, filed on Oct. 16, 2003.

(51) Int. Cl.
    *A61B 5/04*    (2006.01)
(52) U.S. Cl. .................. 600/545; 600/544; 623/25
(58) Field of Classification Search ............... 600/544; 623/25
    See application file for complete search history.

(56) References Cited

U.S. PATENT DOCUMENTS

| | | | |
|---|---|---|---|
| 6,171,239 B1 | 1/2001 | Humphrey | 600/372 |
| 6,609,017 B1 | 8/2003 | Shenoy et al. | 600/372 |
| 6,615,076 B1 | 9/2003 | Mitra et al. | 600/544 |
| 6,731,964 B1 * | 5/2004 | Shenoy et al. | 600/372 |
| 2003/0023319 A1 * | 1/2003 | Andersen et al. | 623/24 |
| 2003/0078552 A1 | 4/2003 | Mitra et al. | 600/587 |

OTHER PUBLICATIONS

"An Analysis of neural receptive field plasticity by point process adaptive filtering" Brown et al. PNAS Oct. 9, 2001, vol. 98, No. 21, pp. 1221-12266. www.pnas.org/cgi/doi/10.1073/pnas.201409398.*

EE. Fetz "Real-time control of a robotic arm by neuronal ensembles" *Nature Neuroscience* vol. 2, No. 7 pp. 583-584, Jul. 1999.

(Continued)

*Primary Examiner*—Robert L. Nasser
*Assistant Examiner*—Patricia Mallari
(74) *Attorney, Agent, or Firm*—Lumen Intellectual Property Services, Inc.

(57) ABSTRACT

A brain machine interface for decoding neural signals for control of a machine is provided. The brain machine interface estimates and then combines information from two classes of neural activity. A first estimator decodes movement plan information from neural signals representing plan activity. In one embodiment the first estimator includes an adaptive point-process filter or a maximum likelihood filter. A second estimator decodes peri-movement information from neural signals representing peri-movement activity. Each estimator is designed to estimate different aspects of movement such as movement goal variables or movement execution variables.

20 Claims, 10 Drawing Sheets

OTHER PUBLICATIONS

J.P. Donoghue "Connecting cortex to machines: recent advances in brain interfaces" *Nature Neuroscience Supplement* vol. 5, pp. 1085-1088, Nov. 2002.

M.A.L. Nicolelis "Action from thought" *Nature* vol. 409, No. 18, pp. 403-407, Jan. 2001.

D.M. Taylor, S.I. Helms-Tillery, and A.B. Schwartz, "Direct cortical control of 3d neuroprosthetic devices," *Science*, vol. 296, No. 3, pp. 1829-1832, Jun. 2002.

J. Wessberg et al., "Real-time prediction of hand trajectory by ensembles of cortical neurons in primates," *Nature*, vol. 208, pp. 361-365, Nov. 2000.

J.K. Chapin et al., "Real-time control of a robot arm using simultaneously recorded neurons in the motor cortex," *Nature Neuroscience*, vol. 2, No. 7, pp. 664-670, Jul. 1999.

C. Harris and D. Wolpert, "Signal-dependent noise determines motor planning," *Nature*, vol. 394, pp. 780-784, Aug. 1998.

B. Hoff, "A model of duration in normal and perturbed reaching movement," *Biological Cybernetic*, vol. 71, No. 6, pp. 481-488, Oct. 1994.

C. Koch, *Biophysics of Computation*, Oxford University Press, 1999.

A.P. Batista and R.A. Andersen, "The parietal reach region codes the next planned movement in a sequential reach task," *Journal of Neurophysiology*, vol. 85, No. 2, pp. 539-544, Feb. 2001.

J. Messier and J. Kalaska, "Covariation of primate dorsal premotor cell activity with direction and amplitude during a memorized-delay reaching task," *J. Neurophysiology*, vol. 84, No. 1, pp. 152-165, Jul. 2000.

E. Todorov, "Direct cortical control of muscle activation in voluntary arm movements: a model," *Nature Neuroscience*, vol. 3, No. 4, pp. 391-398, Apr. 2000.

A.P. Georgopoulos, A.B. Schwartz, and R.E. Kettner, "Neuronal population coding of movement direction," *Science*, vol. 233, No. 4771, pp. 1416-1419, Sep. 1986.

B. Amirikian and A. Georgopoulos, "Directional tuning pro-files of motor cortical cells," *Neuroscience Res.*, vol. 36, No. 1, pp. 73-79, Jan. 2000.

E. Brown et al., "Statistical paradigm for neutral spike train decoding applied to position prediction from the ensemble firing patterns of rat hippocampal place cells," *J. Neuroscience*, vol. 18, No. 18, pp. 7411-7425, Sep. 1998.

K. Zhang et al., "Interpreting neuronal population activity by reconstruction: Unified framework with application to hippocampal place cells," *J. Neurophysiology*, vol. 79, No. 2, pp. 1017-1044, Feb. 1998.

N. Twum-Danso and R. Brockett, "Trajectory estimation from place cell data," *Neural Networks*, vol. 14, No. 6-7, pp. 835-844, Jul. 2001.

\* cited by examiner

DECODING OF NEURAL SIGNALS FOR MOVEMENT CONTROL

CROSS-REFERENCE TO RELATED APPLICATIONS

This application is cross-referenced to and claims priority from U.S. Provisional Application 60/512,292 filed Oct. 16, 2003, which is hereby incorporated by reference.

STATEMENT REGARDING FEDERALLY SPONSORED RESEARCH OR DEVELOPMENT

The present invention was supported in part by grant number MARCO contract #2001-CT-888, DARPA Contract #MDA972-02-1-0004 and a National Science Foundation grant No. 1036761/EEC-9402726. The U.S. Government has certain rights in the invention.

FIELD OF THE INVENTION

The present invention relates generally to signal processing in brain machine interfaces. More particularly, the present invention relates to decoding neural activity related to movement planning and execution for prosthetic devices.

BACKGROUND OF THE INVENTION

An exciting emerging field of signal processing is the decoding of neural signals drawn directly from the brain. One of the goals pursued in the field is to restore function to patients with paralyzed limbs through a direct interface with the brain. This interface is also referred to as a brain machine interface. To achieve the goal of developing brain machine interfaces, a signal processing interface must be developed which decodes neural activity. The decoded neural signals could then be used as control signals to control a prosthetic device and restore function. For an overview of the state of this art, the reader is referred to references [R1-R3].

A typical approach to investigating neural coding of motor control has been to use microelectrodes to record the activity of an ensemble of neurons while also recording the related arm movements ([1–3]). Neural activity immediately preceding or simultaneous with arm movements is termed "peri-movement." These signals are often highly correlated with electrically measured muscle activity, suggesting they correspond to muscle control signals. In some brain regions, there is also neural activity long before, or even without, actual movement. This is termed "plan" activity because of its association with intended movements. In the motor and pre-motor cortical regions of the brain, it is common to find neural activity of both types. Thus, in a situation where it is not possible to pre-select the type of neural activity, it is desirable to consider the optimal use of the data gathered, whether plan or peri-movement or both. One might anticipate that combining plan activity with peri-movement activity would improve the accuracy of the reconstructed endpoint of the movement since the plan activity provides additional information as to where the movement should come to rest. Accordingly, the art is in need of new developments of decoding neural signals for movement control.

SUMMARY OF THE INVENTION

The present invention provides a brain machine interface for decoding neural signals for movement control of a machine such as a prosthetic device. The brain machine interface estimates and then combines information from two classes of neural activity. A first estimator decodes movement plan information from neural signals representing plan activity. In one embodiment, the first estimator includes an adaptive point-process filter or a maximum likelihood filter. A second estimator decodes peri-movement information from neural signals representing peri-movement activity. Each estimator is designed to estimate different aspects of movement. For example, the plan (first) estimator is designed to specify movement goal variables such as target position of a limb movement, whereas the peri-movement (second) estimator is designed to specify movement execution variables (e.g., time-varying positions, accelerations, and/or velocities). The next step is to ensure that the outputs of both estimators are in the same space so that they can be combined and outputted as control signals for the machine in the brain machine interface. The transformation(s), if required, and combining the plan and peri-movement information occurs in a combiner. The ultimate control signals are typically defined in movement space.

BRIEF DESCRIPTION OF THE DRAWINGS

The objectives and advantages of the invention will be understood by reading the following detailed description in conjunction with the drawings, in which:

FIG. 2 shows arm movement trajectories for reaches to three different end points. Movement trajectories are stereotyped with roughly sigmoidal position curves (solid lines) and roughly Gaussian velocity curves (dashed lines). Movement trajectories were generated using Equations (1) and (2). Also shown are responses of two neurons, one a plan neuron and one a peri-movement neuron associated with a 0.5 m rightward arm movement. Five representative repetitions, or trials, appear for each neuron with a vertical line indicating the time the simulated neuron emitted an action potential. The dotted line indicates when neural activity was not simulated since it was not needed for the algorithm. Note that plan neural activity is present throughout the simulated plan period (−100 to 0 ms) and the peri-movement neural activity increases and decreases according to the current arm movement velocity (rightward peri-movement preferred directions chosen to ensure positively correlated firing). Spike trains were generated with Equations (5) and (6).

The parameters for the edge detection are ($t_{\zeta 0}$, $t_{gap}$, $t_{\zeta 1}$)= (50,10,15) ms and the threshold is set at 1.25 a.u.

DETAILED DESCRIPTION

Although the following detailed description contains many specifics for the purposes of illustration, anyone of ordinary skill in the art will readily appreciate that many variations and alterations to the following exemplary details are within the scope of the invention. Accordingly, the following embodiment of the invention is set forth without any loss of generality to, and without imposing limitations upon, the claimed invention.

1. General Overview

The brain machine interface of the present invention combines information from two classes of neural activity to estimate control signals for the control of a prosthetic device and restore function. The first class of neural activity is plan activity and relates to movement plans or intentions, i.e., neural activity present before or even without movement. The second class of neural activity is peri-movement and relates to ongoing movement parameters, i.e., neural activity present during movements. The brain machine interface could be implemented using computer devices, chip devices, analog devices, digital devices and/or in computer coded language(s). Such approaches, devices, techniques and languages are common in the art.

Figure 1:
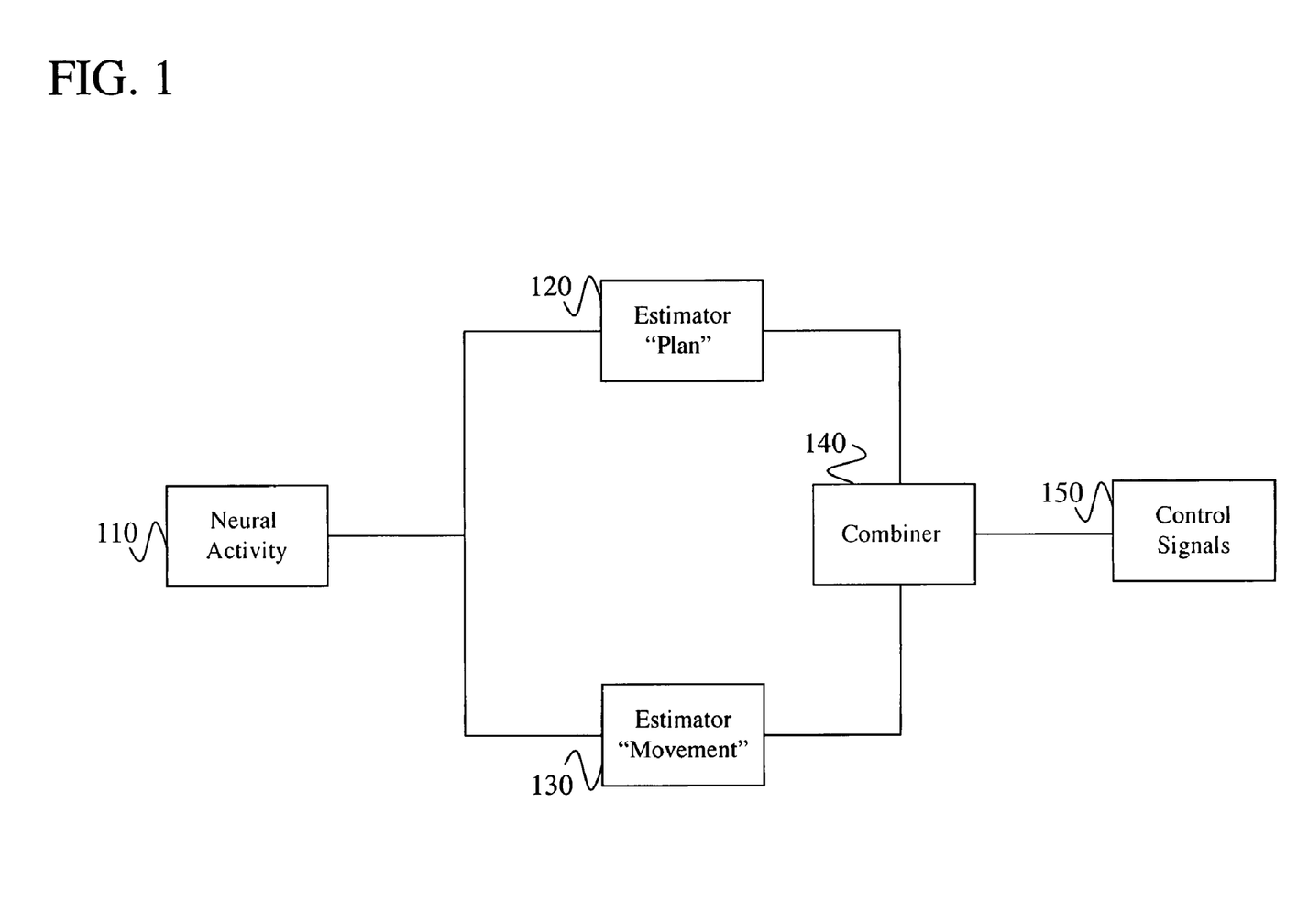
FIG. 1 shows a general overview of the present invention.

Neural activity 110 representing plan and peri-movement is obtained from the brain (e.g., motor and pre-motor cortical regions) as shown in FIG. 1. The art teaches several ways to obtain neural signals from the brain all of which are possible candidates to provide neural input to the brain machine interface of this invention. The obtained neural activity is fed into two parallel estimators 120, 130. Estimator 120 decodes plan activity information from neural activity 110. This estimator decodes movement intention from related plan activity while remaining robust to the possibility of changes in this intention. Estimator 130 decodes peri-movement activity information from neural activity 110. In general, each estimator is designed to estimate different aspects of movement. For example, the plan estimator 120 is designed to specify the goal of a limb movement, such as target position, based on neural activity. However, the plan estimator is not limited to target position since it could also specify quickness or curvature of the movement. Peri-movement estimator 130 is designed to specify movement execution variables (e.g., time-varying positions, accelerations, and/or velocities) based on neural activity. The next step is to ensure that the outputs of both estimators are in the same space so that they can be combined and outputted as control signals 150. Examples of control signals are time varying kinematic and kinetic variables such as endpoint variables of a limb (e.g. an arm), joint motions (position and velocity), joint torques, or the like. The transformation(s) and combining occurs in combiner 140. The ultimate control signals 150 are typically defined in movement space of the machine (e.g. the parameter space of the arm). In one aspect one could transform the output of the plan estimator 120 to movement space and combine those together as control signals 150. In another aspect one could transform the output of the movement estimator 130 to plan (goal) space and combine those. However, since this combination is defined in goal space, one would need to perform an additional transformation to transform the combined movement goal space to movement space before it can be outputted as control signals 150. The following sections describe a detailed implementation of the invention with respect to arm movements.

2. Models

2.1. Movement Model

During quick reaching movements, the hand travels to its target in stereotyped trajectories. In trying to create a model of the brain's control algorithms, various constraints, e.g. minimizing jerk, torque change, transit time, have been proposed, and a recent unifying result suggests that the brain optimizes noisy force signals in order to minimize end-point error [4]. This invention encompasses a model for reaching movements observed in nature. In the specific embodiment reaching movement have been restricted to two dimensions—as when a hand moves on the surface of a touch screen. Furthermore, movements are fully specified by their endpoint (i.e. curved trajectories and multiple speeds are precluded). Finally, trajectories are simplified to have the shape resulting from minimizing the "jerk" (time derivative of acceleration) of the movement [5]. This form is given as $$x(x_f, t) = x_f \cdot \left( 6\left(\frac{t}{t_f}\right)^5 - 15\left(\frac{t}{t_f}\right)^4 + 10\left(\frac{t}{t_f}\right)^3 \right) \quad (1)$$

where $x_f$ is the target location relative to the origin and $t_f$ is the duration of movement, which is further constrained by a smoothness parameter, S, as below.

$$t_f = (60\|x_f\|)^{\frac{1}{3}} S \quad (2)$$

Figure 2:
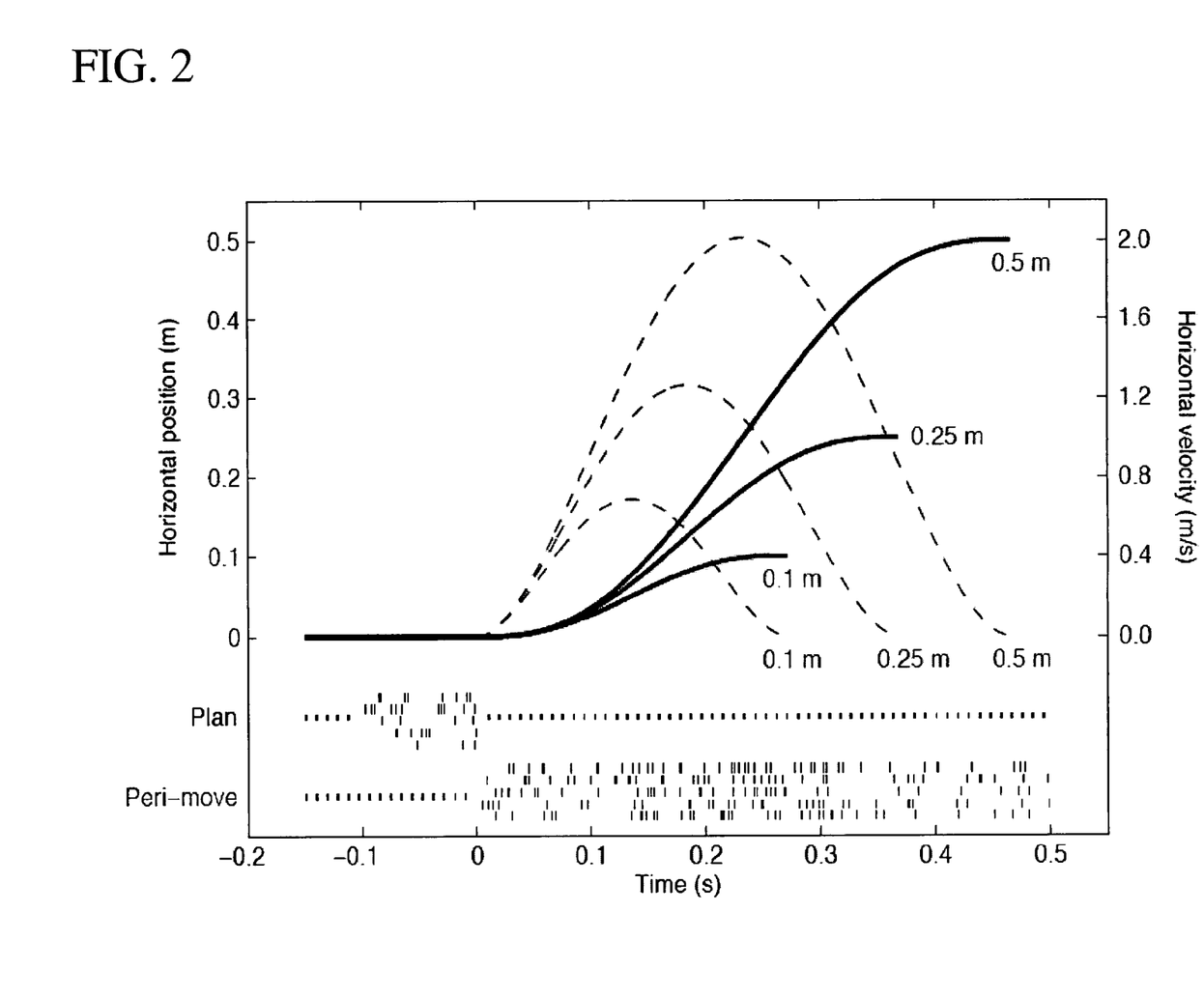

The horizontal components of three sample arm trajectories and their corresponding time derivatives are shown in FIG. 2.

2.2 Neural Signal Model

In experimental neurophysiology the standard technique is to record the time that a neuron emits a stereotypical electrical pulse, referred to as an action potential or "spike." The resulting data constitute a point process time series. The bottom panel of FIG. 2 shows data that might be gathered from two types of neurons during repeated reaches following the longest trajectory (0.5 m rightward reach) in the figure. It has been shown that modeling neurons as firing randomly in time as an inhomogeneous Poisson point process captures most of the statistical variation of neural firing [6]. Thus, the distribution of the number of action potentials, k, observed within a time window of duration T is given by $$p(k) = \frac{1}{k!} \left( \int_t^{t+T} \lambda(\tau) d\tau \right)^k e^{-\int_t^{t+T} \lambda(\tau) d\tau} \quad (3)$$

$$= \frac{(f_T)^k}{k!} e^{-f_T} \quad (4)$$

where $f_T$ is the integral of $\lambda(t)$, the instantaneous rate of the process, over the time window. In our model, the instantaneous rate encodes the parameters of interest, namely arm velocity or target location. The variation of the rate at which a neuron produces spikes as a function of some external parameter is known as its "tuning." In some cases of interest, the parameter may represent a system state variable, for example a planned target. In these cases, the tuning is constant over some period of interest, and the decoding problem reduces to estimating the constant variable of interest from an observed time series of spikes. Alternatively, the tuning may vary with time, as, for example, when it is correlated with movement forces. In this case, the decoding problem is to estimate the time varying movement that was to be generated by the neural signal. The tuning of the subclass of neurons that are involved in planning movements appears to be roughly constant over an interval during which the subject prepares to move. While the tuning of plan neurons has not been as extensively investigated as that of movement neurons (described below), it has been shown that the tuning varies with direction and extent of movement ([7], [8]). In this example of the model the tuning was Gaussian, whereby the firing of the neuron decreases radially from a preferred location. However, other linear and/or non-linear tuning could also be used. The functional form is given as $$f_{planner}(x_f) = T_{plan} \lambda_{max} \exp\left( -\frac{\|x_f - u_{preferred}\|^2}{2\sigma^2} \right) \quad (5)$$

where $f_{planner}$ is the mean of the Poisson process over the duration of the plan interval $T_{plan}$, $\lambda_{max}$ specifies the maximum firing rate of the neurons, $\sigma$ the standard deviation of the tuning, and $u_{preferred}$ the location of maximal firing. It is interesting to note that, unlike the other parameters, which describe biological phenomena, the duration of the plan interval is variable at the system level. In this embodiment, the same values for $\lambda_{max}$ and $\sigma$ are taken for every neuron in our population; u is randomly chosen within the workspace for each neuron. $\lambda_{max}$ and $\sigma$ are typically estimated from data.

The tuning of motor cortical neurons is a matter of some controversy among researchers in the field. Neurons fire proportionally to many variables, including hand velocity, hand force, and muscle forces within the arm [9]. Under many circumstances, observed firing rates vary with the cosine of the angle between hand velocity and some preferred direction. The rates also vary with hand speed. The model for peri-movement neural activity is often dubbed "cosine-tuning" [10]. Note that unlike the plan neurons, the firing of the peri-movement neurons is time-varying. In this embodiment, after digital sampling, the mathematical representation of the sampled Poisson process mean, $f_{mover}$, is $$f_{mover}(x_f, n) = \Delta_t \frac{\lambda_{max} - \lambda_{min}}{2} \cdot \left( \frac{\hat{e}_{preferred} \cdot \dot{x}(x_f, n)}{\|v_{max}\|} + 1 \right) + \Delta_t \lambda_{min} \quad (6)$$

where $\Delta t$ is the time quantization, $\lambda_{min}$ (estimated from data) specifies the minimum firing and $x(x_f,n)$ is the average velocity of the trajectory over $[n\Delta t; (n+1)\Delta t]$, as given by the time derivative of Equation (1). Finally, $\hat{e}_{preferred}$ is a unit vector in the preferred motion direction of the neuron and estimated from data. Studies of peri-movement neural activity in the motor cortex have shown that the directional tuning can also be modeled with more complex functional forms [11].

3. Decoding 3.1. Approach

Previous work in decoding the neural activity associated with arm movements has focused primarily on the peri-movement neural signals. Several approaches have been taken. The most popular ones estimate the velocity (or position) of the arm from affine combinations of the observed firing of the neurons during windows in time [2]. For comparison with the algorithm presented here in this invention, we use the minimum mean-square error filter derived from the preferred directions of the peri-movement neurons. If one rewrites Equation (6) for neuron i as $$f_i(n) = A\hat{e}_i \cdot v(n) + B \quad (7)$$

then, given the observed firing of N neurons concatenated into a column vector f, the standard linear unbiased estimator for v (the time derivative of Equation 1) is given by $$\hat{v} = \frac{1}{A}(E^T E)^{-1} E^T (f - B) \qquad (8)$$

where E is a matrix formed from the concatenation of the preferred directions of the neurons. The trajectory of the arm can be reconstructed by summing the estimated velocities. A strength and weakness of this type of algorithm is that it is agnostic to stereotyping of arm movements, such as those observed in nature and described above. Therefore, it generates an estimate based only on the currently observed (or in more complicated versions, nearby) samples of data.

For neural activity a sample-based algorithm is the "point-process" filter [12]. This filter resembles the philosophy embodied in the well-known Kalman filtering framework. The point-process filter by Brown et al. [12] estimates constant or slowly varying neural activity well, but an estimation algorithm specifically designed to track constant hold periods as well as rapidly changing (time varying) periods has not been put forth. This would be necessary for situations where movement goals are planned and (abruptly) change. Therefore, the present invention proposes an adaptive point-process filter specifically for plan activity with an adaptive parameter that is typically set at a value ($\zeta_0$) well-suited for estimating constant movement goals, but can be briefly switched to a value ($\zeta_1$) well-suited for tracking during rapidly changing periods. The switch to the alternate $\zeta_1$ parameter is governed by a neural-plan activity edge detector algorithm running in parallel to the estimation filter. More details are described in sections 5 and 6. In situations where the movement goal is constant an alternate implementation is also possible as described in section 3 and 4.

3.2. Maximum Likelihood

Figure 3:
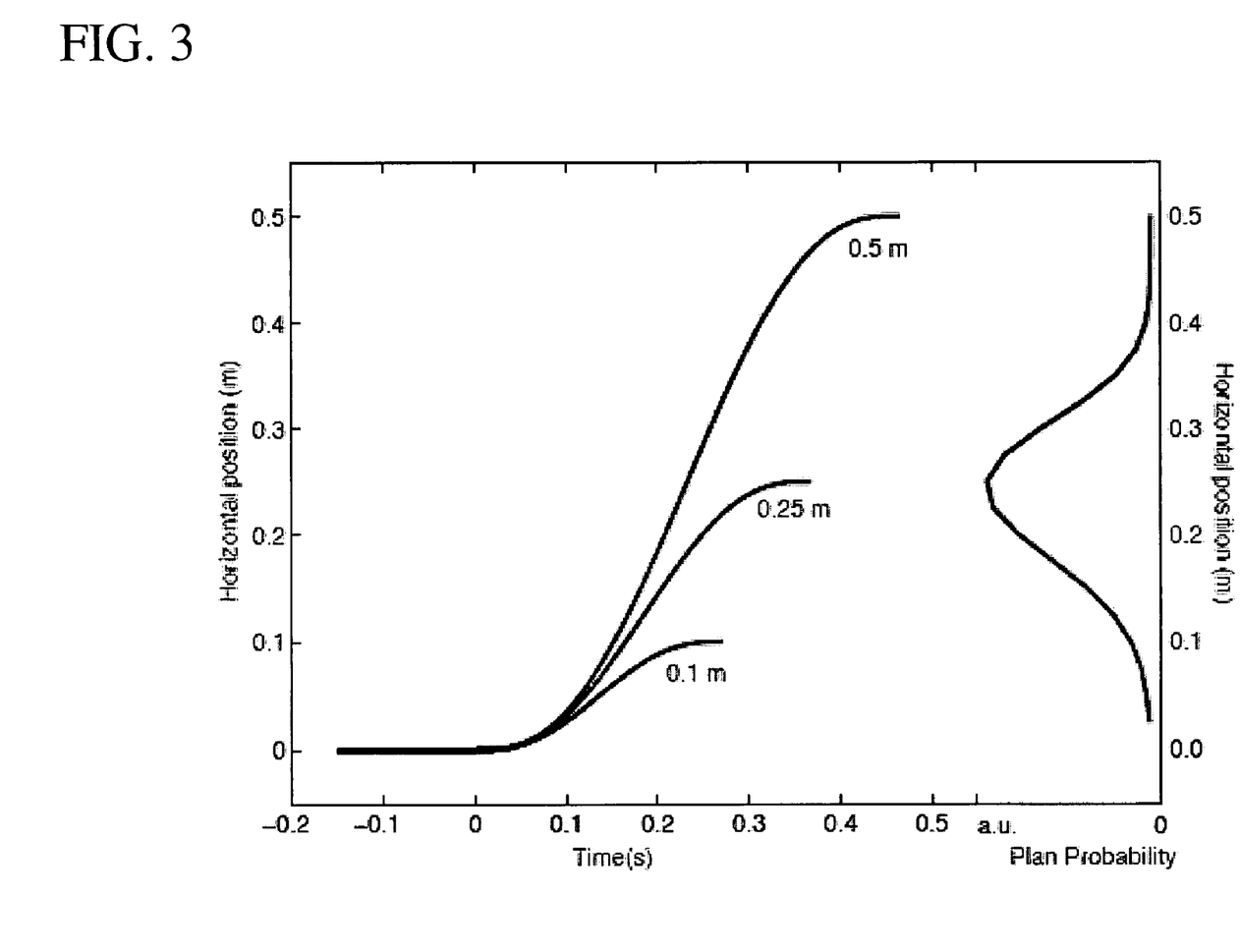
FIG. 3 Neural plan activity imposes an a priori distribution on movement trajectory. Three movement trajectories, as shown in FIG. 2, appear to the left. Neural plan activity can be used to compute a probability distribution function for where the reach will end (curve to the right). The probability distribution is maximum for a 0.25 meter rightward reach, thus at each time step, the point along the trajectory marked 0.25 m is more likely to be correct than the points corresponding to that time step on the other two trajectories.

The previous observation that certain classes of movements are stereotyped suggests that greater accuracy may be achieved by holistically treating the neural firing as a temporal sequence of values specified by the endpoint of the movement rather than isolated samples. For peri-movement neurons, we can write the log-likelihood of arm position at any time as $$LL(x_f, n) = \log\left[\prod_{j=1}^{M} \prod_{\tau=1}^{n} p(k_{mover,j}(\tau) | x_f)\right] \qquad (9)$$

where $k_{mover,j}$ is the number of spikes observed from peri-movement cell j and $p(k_{mover,j}(\tau)|x_f)$ is found by substituting Equation (6) into (4). Due to the assumption that endpoints fully specify trajectories, the maximum likelihood estimate is $$\hat{x}_{est}(n) = x\left(\operatorname*{argmax}_{x_f}[LL(x_f, n)], n\Delta_t\right) \qquad (10)$$

where $x(x_f, t)$, the trajectory inverse function that maps from an endpoint to the point along the trajectory at time t, is found in Equation (1). Equations (9) and (10) illustrate that the estimate of the current arm position is generated by evaluating which of a family of arm trajectories—indexed by the movement endpoint—best fit the current data, and then choosing the current position of that trajectory for the current estimate. Furthermore, if the data presented to the decoding system is composed of both plan and peri-movement neural activity, the integration of the plan activity is seamless. As shown in FIG. 3, because of our stereotypical movement assumptions, plan activity (right panel), which is tuned for the endpoint of a movement, effects an a priori distribution on the possible trajectories (left panel) that may be decoded from peri-movement neural activity. The new log likelihood function is $$LL_{full}(x_f, n) = \log\left[\prod_{i=1}^{P} p(k_{planner,i} | x_f)\right] + LL_{mover} \qquad (11)$$

where $k_{planner,i}$ is the number of spikes observed from plan cell i and the likelihood surface corresponding to this neural activity has been added to the log-likelihood of Equation (9). To evaluate the maximum likelihood, Equation (11) is substituted into (10). Notice that the estimate can also be formed without peri-movement activity, corresponding to $LL_{mover}=0$. By using small time windows, the analysis can be simplified. In the short interval limit, a Poisson process becomes a Bernoulli process, i.e. produces only zero or one as an outcome. Inserting the probability distribution in this case yields the following likelihood function.

$$LL(x_f, t) = C + \sum_{i=1}^{P}(k_i \log[f_{planner,i}(x_f)] - f_{planner,i}(x_f)) + \qquad (12)$$
$$\sum_{\tau=1}^{n}\sum_{j=1}^{M}(I_j(\tau)\log[f_{mover,j}(x_f, \tau)] - f_{mover,j}(x_f, \tau))$$

where for neuron i, $k_i$ is the number of spikes observed, and $f_i$ is the tuning as a function of target location (given in Equations (5) and (6)), I is an indicator function for the firing of a cell, and P and M are the numbers of plan and peri-movement neurons, respectively. Because there is no closed form solution to this maximization problem, the actual solution is approximated in our model through an exhaustive search through discretized space.

4. Results 4.1. Architecture

Figure 4:
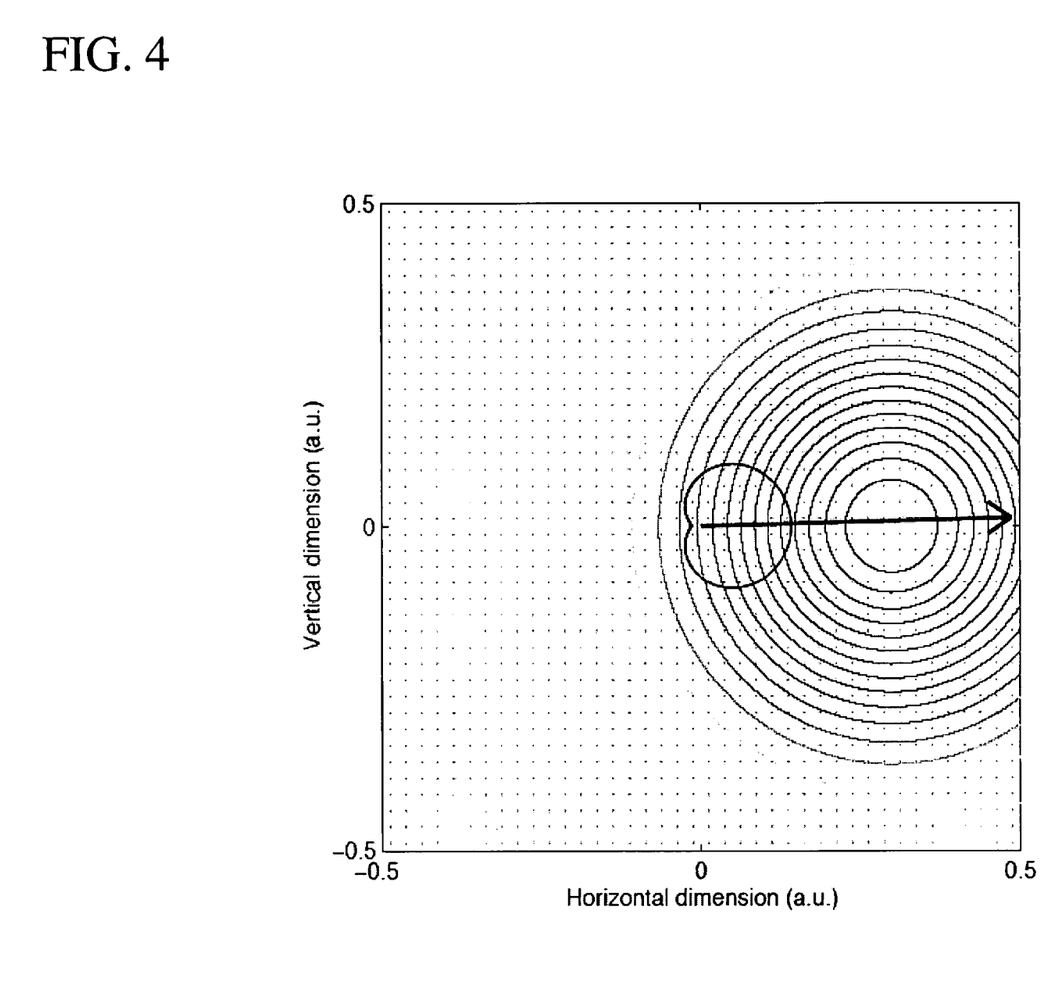
FIG. 4 shows reaching arm movements that were simulated from the center of the workspace to each of the 1600 possible endpoints (array of points). The arrow depicts a rightward and slightly upward reach. The workspace is square and is one arbitrary unit (a.u.) on a side. All distance parameters are consistently measured against this unit. A plan neuron 2-dimensional Gaussian receptive field centered at 0.3 a.u. to the right and is shown as a family of iso-intensity rings. The cosine tuning of a peri-movement neuron, centered in the workspace with a rightward preferred direction, is also shown (solid line). Note that the plan neuron receptive field is drawn to scale while only the shape, not size, of the peri-move neuron movement field has meaning since arm movement velocity modulates the response.

Neural signals were generated for movements to targets chosen at random in a unit square (arbitrary units consistent throughout experiments) centered on zero as in FIG. 4. As discussed above, discretizing the number of potential targets into a grid of endpoints allows for simplified calculation of the maximum likelihood. As decoding errors decrease, the estimated endpoints begin to snap to the grid, causing an abnormal acceleration in the performance of the algorithm. In this embodiment, we utilized a grid of 1600 points. Neuron parameters (e.g. preferred locations for plan neurons, preferred directions for peri-movement neurons) were randomized with the decoding process typically repeated over at least 20 sets. For each set of parameters, at least 200 random targets were typically selected. Reaches to these endpoints were constructed by Equations (1) and (2) where the smoothness parameter, S, was chosen such that a reach to the farthest target in the grid took 0.5 seconds. Random neural firing data were generated with a time quantization of 1 millisecond using the methods and probability distributions described previously.

4.2. Plan and Peri-Movement

For unbiased estimators, the variances of estimates from independent observations add inversely. In this particular case, one can think of each neuron as providing an independent observation. Thus, in the biologically plausible range of parameters, we would expect an error model such as $$\frac{1}{E[(\hat{x}-x)^2]} \propto \frac{1}{\sigma_{plan}^2} N_{plan} + \frac{1}{\sigma_{move}^2} N_{move} - C(N_{plan}, N_{move}) \quad (13)$$

where $N_{plan}$ and $N_{move}$ are the number of plan neurons and peri-movement neurons, respectively, and $\sigma_{plan}^2$ and $\sigma_{move}^2$ represent the contribution of a single neuron to the mean square estimation error. The final term represents the non-linear portion of the error (discussed below). It can be shown that the variance of the maximum-likelihood estimate of the parameter of a Poisson process varies inversely with the length of the estimation window [14]. It is expected that the single-neuron variance of plan neurons will be inversely proportional to the duration of plan interval.

For small numbers of neurons chosen randomly, the typical distribution of neurons in the workspace (preferred locations or directions) will be non-uniform (e.g. the preferred directions will be closer to each other than to orthogonal, or the preferred locations will be unbalanced in workspace coverage). The result is higher than expected error. This is the source of the C( . . . ) term in Equation (13). The performance of the prosthetic system with limited numbers of neurons is of special interest, since current instrumentation only permits interfacing with small neural populations (10s–100s of cells). Furthermore, the performance of systems controlled by even small numbers of neuron may be further enhanced by the brain's ability to adapt through time [1].

Figure 5:
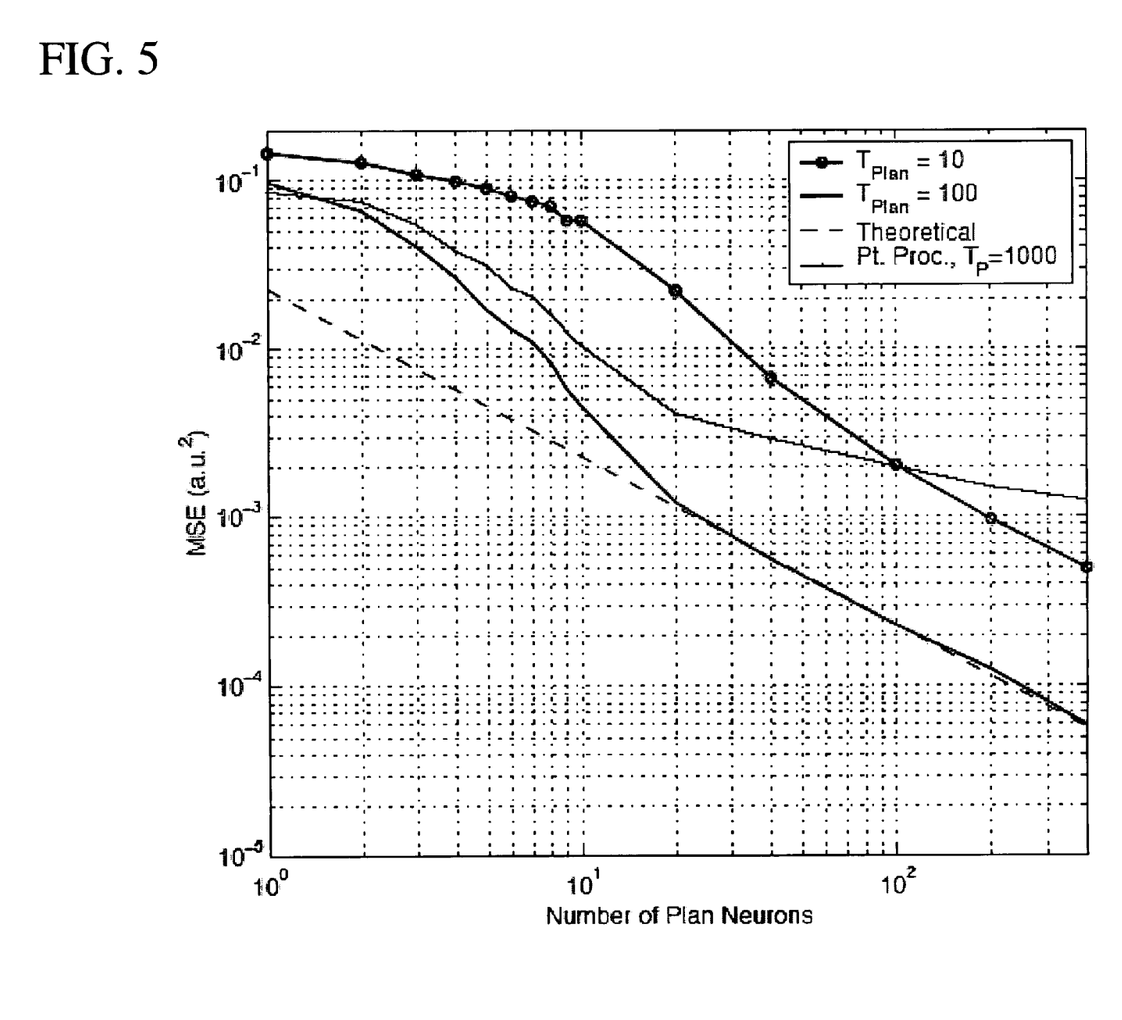
FIG. 5 shows decoded trajectory error as a function of the number of plan neurons. At least 100 random endpoints were chosen for each of at least 20 randomly parameterized ensembles of neurons ($\sigma$=0.2 a.u., $\lambda_{max}$=100 and $\lambda_{min}$=10 spikes/second, consistently throughout this study). The dotted line depicts a fit of the many neuron limit of system performance. The thin line shows the performance of a point process filter on the same data (random walk variance=0.001 a.u.$^2$).

FIG. 5 shows results as the number of plan neurons in the system increases. The error metric is the trajectory error measured as the square distance between estimated and actual hand positions averaged over the movement time. Notice that the error performance is well approximated by Equation (13), not only by decreasing inversely to neuron count, but also by scaling inversely with the length of the plan interval. If we take the value for 200 neurons as characteristic of the many neuron limit, the data suggest that $\sigma_{plan}^2$ is approximately 0.0025 a.u.$^2$ sec—i.e. 0.25 a.u.$^2$ for 10 msec plan or 0.025 a.u.$^2$ for 100 msec plan. We found that, in the many neuron limit, this value was inversely related to the tuning width of the neurons. For example, for a standard deviation of 0.4 a.u.$^2$, twice that used in our experiments, the per-neuron variance was measured as 0.0051 a.u.$^2$ sec. For a standard deviation of 0.1 a.u.$^2$, the per-neuron variance was measured as 0.0021 a.u.$^2$ sec.

The plan interval parameter ($T_{plan}$ in Equation (5)) is important to system designers since it can be used to reduce the contribution of the planner neurons to overall estimator variance. As seen in Equation (13), the planner population variance can be reduced in two ways: by decreasing $\sigma_{plan}^2$ or increasing the number of neurons ($N_{plan}$). The former can be achieved by increasing $T_{plan}$; training the user to extend the period during which a movement is planned. The number of neurons interfaced cannot be easily increased to a fixed number of electrodes have been implanted in the subject.

Figure 6:
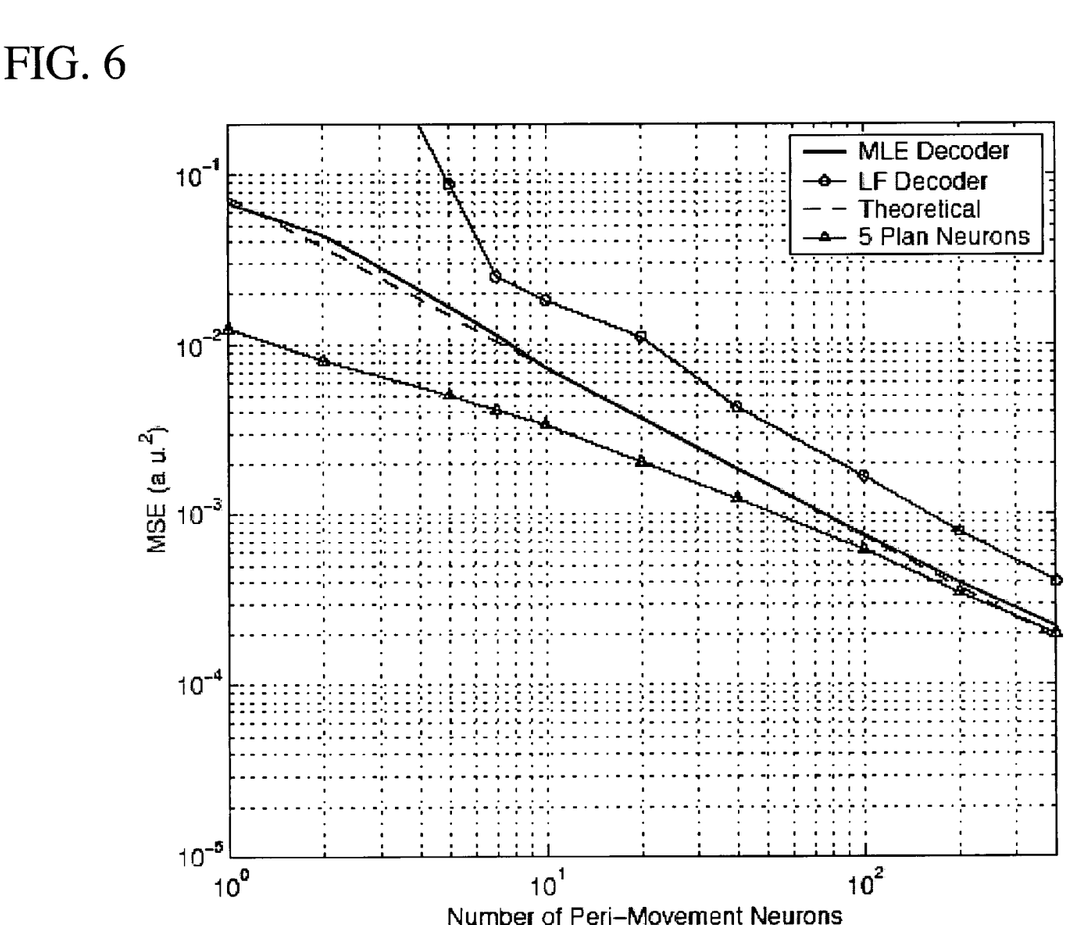
FIG. 6 shows decoded trajectory error as a function of the number of peri-movement neurons. The performance of the maximum likelihood decoder is compared with the theoretical bound, a linear filter, and a system in which the decoder uses not only peri-movement neural activity, but also information from 10 plan neurons.

FIG. 6 shows the dependence of trajectory error on the number of peri-movement neurons. As expected, the inverse relationship of Equation (13) holds. In this case, $\sigma_{move}^2$ is approximately 0.076 a.u.$^2$. Thus, in the limit of many neurons, the information gained from a plan neuron with a plan interval of about 30 ms is equivalent to that gained from a peri-movement neuron. Also shown is a plot of the performance of a system in which the activity from 5 plan neurons is integrated with peri-movement activity. As expected, for small numbers of peri-movement neurons, trajectory error is significantly reduced by the addition of plan activity.

A key difference between the error performance of plan- and peri-movement-based decoding is in their convergence characteristics. The C( . . . ) term of Equation (13) represents the greater error that occurs when there are only a small number of neurons. As the number of plan and peri-movement neurons increases, C( . . . ) tends to zero. As seen in FIG. 6, in peri-movement neurons, when there are more than two, each neuron contributes nearly its full amount of information. Hence, the error for the peri-movement neurons is linear throughout nearly the whole regime of neuron densities.

The error convergence of plan neurons is closely related to the size of workspace area in which the neurons provide significant signal differentiation. Thus, unlike the broadly tuned peri-movement neurons, for the tuning widths used in this experiment, the system error does not converge immediately to its many neuron limit. However, this effect is significantly affected by the tuning width of the neurons. Intuitively, neurons with wide tuning are less specific, hence their limiting variance is higher than those with narrower tuning. For the same reason, for smaller numbers of neurons, those with wide tuning cover more of the workspace, and thus the error converges to the many neuron limit more quickly. Comparing the limiting cases, for infinitely wide tuning the number of neurons has no effect on the error; for infinitely narrow tuning, an infinite number of neurons is needed to decode reaches in a continuous workspace.

Figure 7:
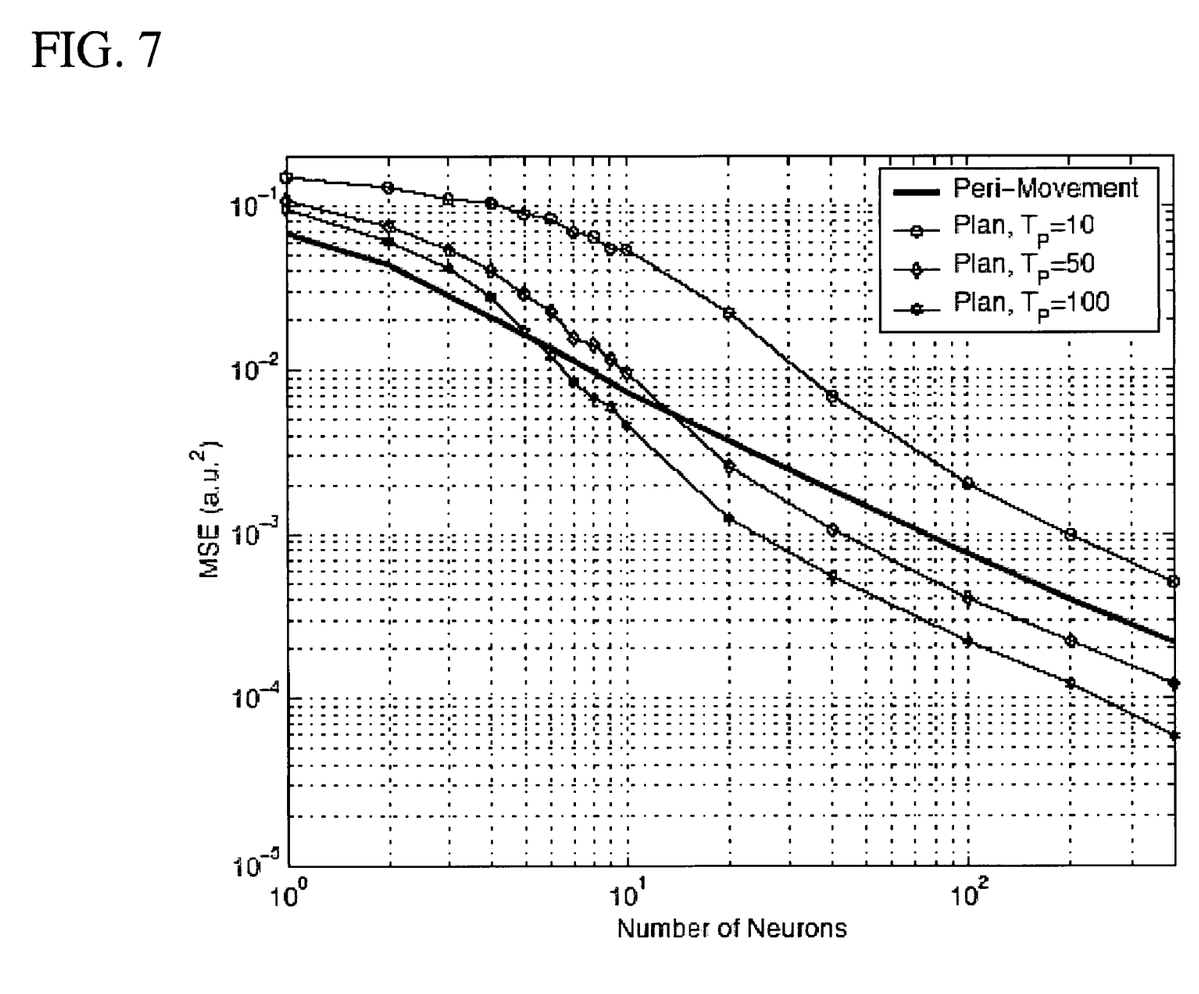
FIG. 7 shows plan- and peri-movement-only decoder performance. Notice different error convergence characteristics of decoders using only plan or peri-movement neural activity. In the limit, only neuron parameters and the number of neurons matter.

FIG. 7 shows three regimes of operation for systems composed of plan and peri-movement neurons. When there are few neurons, peri-movement neurons provide more per-neuron estimating accuracy than plan neurons. This is regime 1—roughly 1–10 neurons in FIG. 7. When there are a large number of neurons, both the peri-movement and plan neurons will cover the entire workspace well. Thus, comparison between the per-neuron variance of plan and peri-movement neurons can be done solely on the basis of system parameters. As shown, a system based only on plan or peri-movement neurons will provide higher decoder accuracy depending on whether $\sigma_{plan}$ or $\sigma_{move}$ is lower. This is regime 3—roughly 10 or more neurons in FIG. 7. When the per-neuron variances are comparable (regime 2—around 10 neurons in FIG. 7), the exact distribution of neuron centers and preferred directions will heavily influence system performance.

5. Adaptive Point-Process Filter

As mentioned above, under some circumstances, the plan activity may undergo abrupt changes, as when the user changes their mind about the desired target location. In such circumstances, the ability to adaptively track time varying changing plan activity is desirable. This is achieved in the present invention achieves by an adaptive point process filter.

The point-process filter uses a recursive algorithm, similar to the Kalman time and measurement updates, to incorporate the previous sample estimate with spike data from the current time point. The previous estimate is first modified by the time update, with the upcoming movement increment vector stochastically distributed as a 2-dimensional Gaussian centered at the past estimate. The constraint is known here as the random walk parameter since the concept was first used to describe the seemingly random movement statistics of a free foraging rat. The measurement update adjusts the estimate by the latest point-process observations. The new estimate is spatially continuous. A variance is calculated with each estimate, thereby allowing the current estimate to be used to form a prior distribution for the next estimate.

Equations (14–15) constitute the one-step prediction (or time update) phase of the point-process filter. The measurement update equations for $\hat{x}(t_k|t_k)$ and posterior variance W $(t_k|t_k)$ equations are not included here. These and further details of the filter derivation can be found in [12].

$$x(t_k) - x(t_{k-1}) \sim N(0, W_x(\Delta_k)); \quad (14)$$

$$\hat{x}(t_k|t_{k-1}) = \hat{x}(t_{k-1}|t_{k-1}); \quad (15)$$

$$W(t_k|t_{k-1}) = W_x(\Delta_k) + W(t_{k-1}|t_{k-1}); \quad (16)$$

Equation (14) describes the prior on $x(t_k)$ given $x(t_{k-1})$. In equation (15), the vector $\hat{x}(t_p|t_q)$ is the position estimate at time $t_p$ given all the information until the $q^{th}$ time step. Equation (16) relates $W(t_k|t_{k-1})$, the variance in the position after the time update, to $W(t_{k-1}|t_{k-1})$, the variance of the preceding estimate $\hat{x}(t_{k-1}|t_{k-1})$. The Gaussian distribution of the random walk in Equation (14) is described by its covariance matrix $W_x(\Delta_k)$; this matrix is constant throughout the operation of the filter. If the diagonal elements of this matrix are small, the prior estimate will be very influential when computing the next estimate. Conversely, the prior estimate will have a smaller effect on the next estimate if the diagonal elements are large. This allows the filter to be nimble when the plan position changes; it will place more importance on the latest vector of spikes at the cost of increasing sensitivity to noise present in the spike train.

The optimal choice for $W_x(\Delta_k)$ is dictated by the statistics of the movement. Consider a simplified version of the random walk covariance where $W_x(\Delta_k) = \zeta^2 I$. If the number of steps per second is reduced (or, equivalently, hold times lengthened) the optimal choice of $\zeta$ would decrease. Similarly, a distribution that favors larger step sizes would prefer a larger value of $\zeta$ than a sequence that has smaller step distances on average. The optimal value of $\zeta$ is termed $\zeta_{opt}$.

To achieve better performance, we can adapt $\zeta$ as follows: use a small random walk parameter ($\zeta_0$) during hold periods and use a larger parameter ($\zeta_1$) to transition between regions of constant plan activity. In this manner, we are able to exploit the benefits of $\zeta_0 < \zeta_{opt}$ without suffering from its corresponding slow switching rate. On the flip side, $\zeta_1 > \sigma opt$ provides a faster switching rate without the penalty of high noise during the constant hold regions.

Therefore, we run two point-process filters in parallel and employ an edge detector. By default, the estimator uses the point-process filter with parameter $\zeta_0$. When the detector finds an edge, the prior estimate and variance of the $\zeta_0$ filter is switched to that of the $\zeta_1$ filter. This operation need only be performed for a single time step. It has the effect of reseeding the slower slewing filter to a position closer to the actual plan position. Given that the estimate is coming from another filter with higher $\zeta^2$, the reseeded position is naturally noisy. This is not a problem—the prior variance is also reseeded, allowing for large corrections until the variance naturally relaxes with the accumulation of enough post-edge data.

5.1 Edge Detection

To test the point-process step tracking algorithms, an edge detector is required. The goal should be to implement a strategy that detects edges with a short latency and minimizes false negatives. It is also beneficial to reduce false positives since these errors can introduce excessive noise into the system. The method used for edge detection is a simple threshold detector. The algorithm is characterized by the parameter tuple $(t_0, t_{gap}, t_1)$. At any instant in time there is $(t_{\zeta_0} + t_{gap} + t_{\zeta_1})$, amount of history in the detection filter. When checking for an edge, the algorithm averages the last $t_{\zeta_0}$ samples from the $\zeta_0$ point-process filter and averages the first $t_{\zeta_1}$ samples from the $\zeta_1$ point-process filter. An edge is declared if the average from the faster response filter exceeds the average from the slower filter by a threshold. After the edge detection, the adaptive point-process algorithm acts as previously described. The parameters for the edge detector, including the threshold, were fixed and could be selected through optimization or selections.

6. Results 6.1 Architecture

Neural tuning function parameters must be estimated from data as mentioned above (section 2.2). In the following embodiment the parameters were specified as follows. We used populations of 100 neurons with preferred locations chosen uniformly randomly in the workspace. The maximal firing rate of each cortical neuron is set to 100 spikes per second. The workspace is a 10 by 10 square of arbitrary units (a.u.) and σ in Equation (5) is chosen so that the area with $\lambda_i(x) \geq 0.5 \lambda_{max}$ covers approximately 40% of the workspace. Again, there is no apparent closed-form solution for the maximum-likelihood filter. Thus, we discretized the workspace into a grid to simulate the maximum-likelihood expanding filter. The following results are from a uniformly spaced 400 point grid. Each trial lasts two seconds in which step sequences are generated as per the described assumptions. The error metric is the average Euclidean distance of the estimate from the true plan position over the entire trial. This is appropriate since we assume that the "go" signal can appear at any time within the trial. Finally, we averaged the trial-by-trial error over 500 iterations to guarantee consistent convergence.

6.2 Non-Adaptive Point-Process Filter

Figure 8:
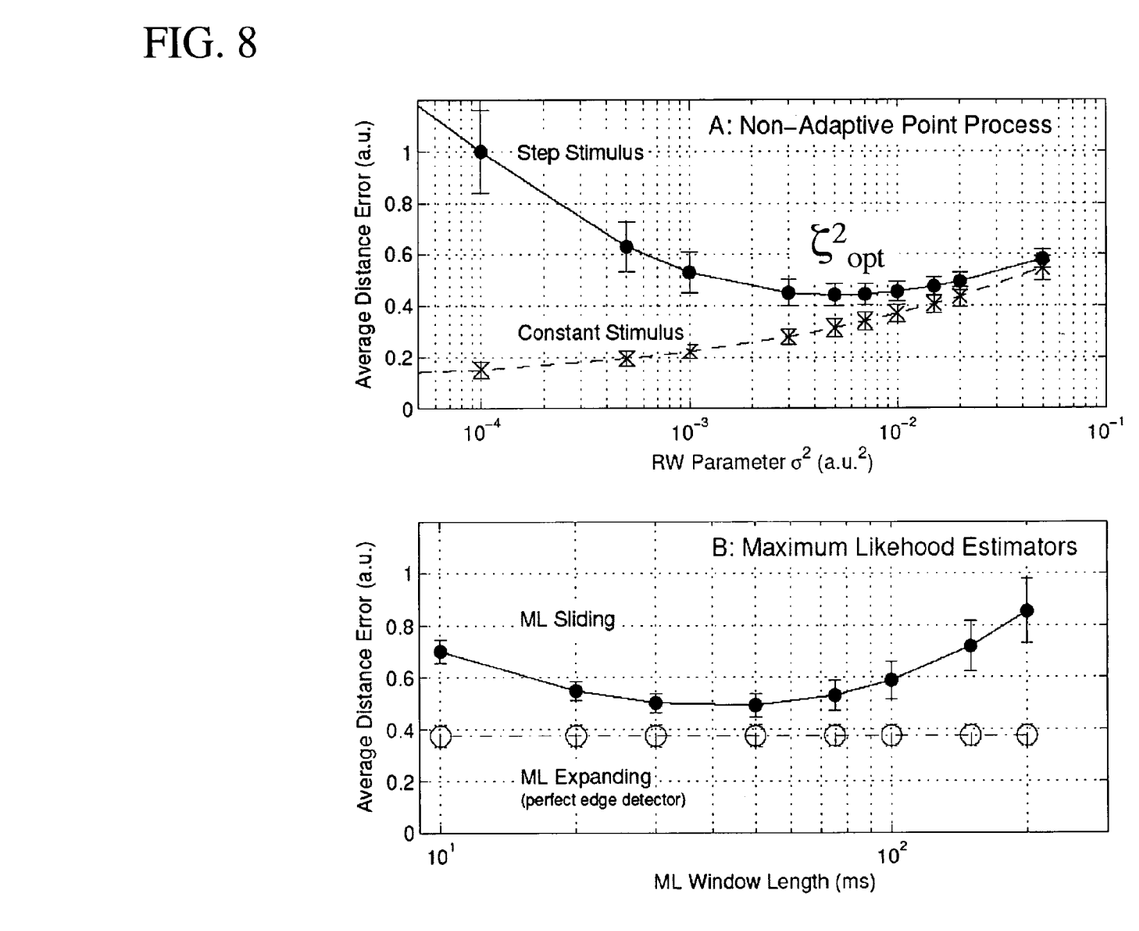
FIG. 8 shows comparison of baseline cases. (A) Performance of the PP filter as a function of a single, fixed random walk parameter. (B) Analogous performance curves for ML filters. Note that the expanding filter is not a function of window size; its error is simply repeated across the x-axis for comparison purposes. Error bars indicate standard deviation.

We first ran experiments to understand the limitations of the non-adaptive point-process filter. FIG. 8 shows two results of the point-process filter. One was conducted without any step sequences (i.e., the plan distance was drawn for only a single reach from the origin and it was held constant throughout the two-second trial). The point-process filter's initial position was seeded at the origin. Clearly the noise drops with lower $\zeta$ parameters; without any steps, there is no penalty for slower slew rates. Furthermore, this curve is a lower bound on the average error. The addition of steps can only add error in the vicinity of each switch time. Next, the inclusion of steps in the plan sequence yields the convex curve in FIG. 8. As expected, very low values of $\zeta$ incur large error due to the inability to slew quickly to new plan locations while higher values of $\zeta$ suffer from noise during the hold regions. The optimal point based on the plan sequence statistics is denoted as $\zeta^2_{opt}$ on the plot.

6.3 Maximum Likelihood Expanding Filter

For time varying plan activity, the maximum likelihood filter is $$\left(\hat{x}_f(t) = \underset{x}{\operatorname{argmax}}(\log\left[\prod_{i=1}^{P} p(k_{planner,i} \mid x_f, T)\right]\right),$$

where T is the period of time over which neural activity is considered. In the sliding window variant of the invention, the neural activity used for the estimate is taken from a period of time of fixed duration relative to the present. This is directly analogous to sections 3 and 4, if the estimate considered is the one generated by the activity of the entire plan period. In the maximum likelihood expanding filter, the period, T, and the corresponding estimate, resets when the edge detector (described in section 6.2) detects that the movement goal has changed. FIG. 8 shows results from two maximum likelihood algorithms.

6.4 Adaptive Point-Process Filter

Figure 9:
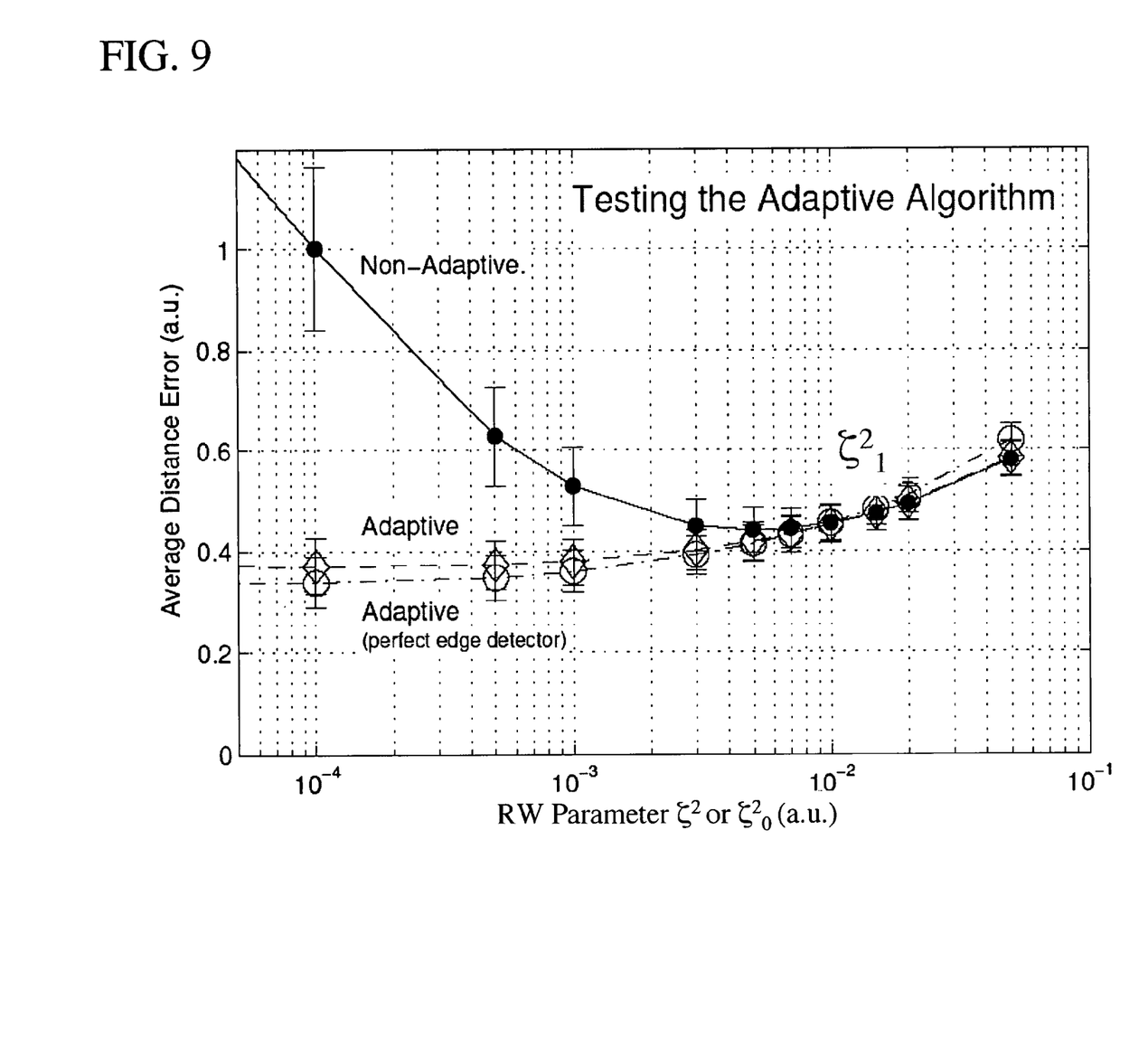
FIG. 9 shows a response of adaptive PP filter. The highest error curve is repeated from FIG. 8A for comparison. For both adapting filters, $\zeta_1$ is fixed to 0.015 a.u.$^2$ and $\zeta_0$ is swept along the x-axis. The lowest curve corresponds to the adaptive point-process filter with a perfect edge detector that has fixed latency of 15 ms. The curve simply labeled "adaptive" shows results that instead use the edge detector algorithm.
Figure 10:
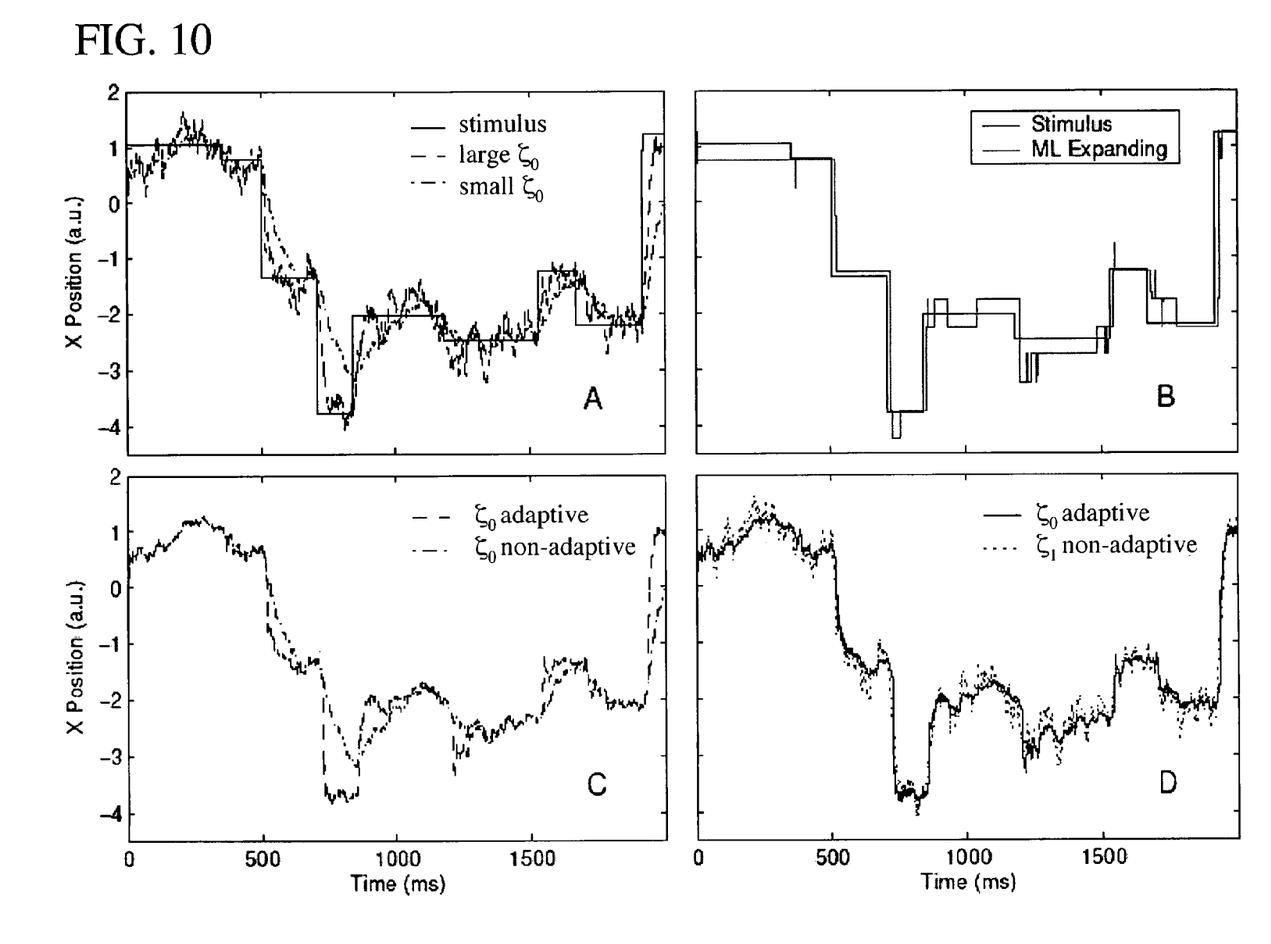
FIG. 10 Shows single trial responses. (A) Illustration of the trade-off between low noise and fast slew rate across different $\zeta$ values. (B) The ML expanding filter looks to be performing well but it suffers from snap-to-grid effects. (C) The asymptotically optimal adaptive PP filter performs much better in terms of slew rate than the non-adaptive filter with $\zeta=\zeta_0$. (D) Furthermore, the adaptive filter outperforms a fixed $\zeta=\zeta_1$ counterpart due to less noise in the hold periods.

The results for the adaptive point-process filter are shown in FIG. 9. We did not perform an exhaustive search of the high-dimensional space of algorithm and model parameters. However, in the regime we tested, there is a marked improvement of our algorithm over the non-adaptive filter. We chose $\zeta_1$ by optimization near the point $\zeta_{opt}$ in FIG. 8. Then, we swept $\zeta_0$ and found that the error is lower with smaller values of $\zeta_0$ (FIG. 9). The difference in error between very low values of $\zeta_0$ is not well differentiated because, after each edge, the injected variance from filter $\zeta_1$ does not decay sufficiently by the time of the next edge. The best value of $\zeta_0$ is tightly coupled with the success statistics of the edge detector since the cost of missing an edge will eventually become more significant to the overall error as $\zeta_0$ decreases. The asymptotic error of 0.37 a.u. at low $\zeta 0$ is approximately 16% better than the average error of 0.44 a.u. from the optimal $\zeta_{opt}$ non-adaptive filter. In a trial-by-trial comparison, 99.2% of all trials show a performance improvement with the adaptive filter. It is also informative to visually inspect the output estimates of these various filters in a single trial (FIG. 10).

7. References

[R1] E. E. Fetz "Real-time control of a robotic arm by neuronal ensembles" *Nature Neuroscience* vol. 2, no. 7 pp. 583–584, July 1999.

[R2] J. P. Donoghue "Connecting cortex to machines: recent advances in brain interfaces" *Nature Neuroscience Supplement* vol. 5, pp. 1085–1088, November 2002.

[R3] M. A. L. Nicolelis "Action from thought" *Nature* vol. 409, no. 18 pp. 403–407, January 2001.

[1] D. M. Taylor, S. I. Helms-Tillery, and A. B. Schwartz, "Direct cortical control of 3d neuroprosthetic devices," *Science*, vol. 296, no. 3, pp. 1829–1832, June 2002.

[2] J. Wessberg et al., "Real-time prediction of hand trajectory by ensembles of cortical neurons in primates," *Nature*, vol. 208, pp. 361–365, November 2000.

[3] J. K. Chapin et al., "Real-time control of a robot arm using simultaneously recorded neurons in the motor cortex," *Nature Neuroscience*, vol. 2, no. 7, pp. 664–670, July 1999.

[4] C. Harris and D. Wolpert, "Signal-dependent noise determines motor planning," *Nature*, vol. 394, pp. 780–784, August 1998.

[5] B. Hoff, "A model of duration in normal and perturbed reaching movement," *Biological Cybernetics*, vol. 71, no. 6, pp. 481–488, October 1994.

[6] C. Koch, *Biophysics of Computation*, Oxford University Press, 1999.

[7] A. P. Batista and R. A. Andersen, "The parietal reach region codes the next planned movement in a sequential reach task," *Journal of Neurophysiology*, vol. 85, no. 2, pp. 539–544, February 2001.

[8] J. Messier and J. Kalaska, "Covariation of primate dorsal premotor cell activity with direction and amplitude during a memorized-delay reaching task," *J. Neurophysiology*, vol. 84, no. 1, pp. 152–165, July 2000.

[9] E. Todorov, "Direct cortical control of muscle activation in voluntary arm movements: a model," *Nature Neuroscience*, vol. 3, no. 4, pp. 391–398, April 2000.

[10] A. P. Georgopoulos, A. B. Schwartz, and R. E. Kettner, "Neuronal population coding of movement direction," *Science*, vol. 233, no. 4771, pp. 1416–1419, September 1986.

[11] B. Amirikian and A. Georgopoulos, "Directional tuning pro-files of motor cortical cells," *Neuroscience Res.*, vol. 36, no. 1, pp. 73–79, January 2000.

[12] E. Brown et al., "A statistical paradigm for neural spike train decoding applied to position prediction from the ensemble firing patterns of rat hippocampal place cells," *J. Neuroscience*, vol. 18, no. 18, pp. 7411–7425, September 1998.

[13] K. Zhang et al., "Interpreting neuronal population activity by reconstruction: Unified framework with application to hippocampal place cells," *J. Neurophysiology*, vol. 79, no. 2, pp. 1017–1044, February 1998.

[14] N. Twum-Danso and R. Brockett, "Trajectory estimation from place cell data," *Neural Networks*, vol. 14, no. 6–7, pp. 835–844, July 2001.

What is claimed is:

1. A brain machine interface, comprising:
   (a) a first estimator to decode movement plan information from neural signals representing plan activity;
   (b) a second estimator to decode peri-movement information from neural signals representing peri-movement activity; and
   (c) a combiner to combine said decoded movement plan information and said decoded peri-movement information into control signals for said machine in said brain machine interface.

2. The brain machine interface as set forth in claim 1, wherein said first estimator comprises an adaptive point-process filter.

3. The brain machine interface as set forth in claim 1, wherein said first estimator comprises a maximum likelihood filter.

4. The brain machine interface as set forth in claim 1, wherein said plan information specifies movement goal variables.

5. The brain machine interface as set forth in claim 1, wherein said peri-movement information specifies movement execution variables.

6. The brain machine interface as set forth in claim 1, wherein said control signals are defined in the movement space of said machine.

7. The brain machine interface as set forth in claim 1, wherein said combiner specifies control signals in the movement space of said machine.

8. A method for estimating movement control signals for a machine in a brain machine interface, comprising:

(a) estimating movement plan information from neural signals representing plan activity;
(b) estimating peri-movement information from neural signals representing peri-movement activity; and
(c) combining said estimated movement plan information and said estimated peri-movement information into control signals for said machine in said brain machine interface.

9. The method as set forth in claim 8, wherein said first estimator comprises an adaptive point-process filter.

10. The method as set forth in claim 8, wherein said first estimator comprises a maximum likelihood filter.

11. The method as set forth in claim 8, further comprising specifying said plan movement information as movement goal variables.

12. The method as set forth in claim 8, further comprising specifying said peri-movement information as movement execution variables.

13. The method as set forth in claim 8, wherein said control signals are defined in the movement space of said machine.

14. A program storage device embodying a program of instructions executable by a computer to perform method steps for estimating control signals for a machine in a brain machine interface, comprising:
(a) estimating movement plan information from neural signals representing plan activity;
(b) estimating peri-movement information from neural signals representing peri-movement activity; and
(c) combining said estimated movement plan information and said estimated peri-movement information into control signals for said machine in said brain machine interface.

15. The program storage device as set forth in claim 14, wherein said first estimator comprises an adaptive point-process filter.

16. The program storage device as set forth in claim 14, wherein said first estimator comprises a maximum likelihood filter.

17. The program storage device as set forth in claim 14, further comprising specifying said plan movement information as movement goal variables.

18. The program storage device as set forth in claim 14, further comprising specifying said peri-movement information as movement execution variables.

19. The program storage device as set forth in claim 14, wherein said control signals are defined in the movement space of said machine.

20. A brain machine interface, comprising:
(a) a prosthetic device;
(b) a filter to decode movement goal information from neural signals representing time-varying plan activity, wherein said filter is an adaptive point process filter or a maximum likelihood filter; and
(c) a controller to control said prosthetic device with said decoded movement goal information.

* * * * *